United States Patent
Eidenschink

(10) Patent No.: US 9,844,435 B2
(45) Date of Patent: Dec. 19, 2017

(54) TRANSAPICAL MITRAL VALVE REPLACEMENT

(71) Applicant: St. Jude Medical, Cardiology Division, Inc., St. Paul, MN (US)

(72) Inventor: Tracee Eidenschink, Wayzata, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 207 days.

(21) Appl. No.: 14/190,496

(22) Filed: Feb. 26, 2014

(65) Prior Publication Data
US 2014/0249621 A1 Sep. 4, 2014

Related U.S. Application Data

(60) Provisional application No. 61/771,439, filed on Mar. 1, 2013.

(51) Int. Cl.
*A61F 2/24* (2006.01)
(52) U.S. Cl.
CPC .......... *A61F 2/2418* (2013.01); *A61F 2/2439* (2013.01); *A61F 2/2457* (2013.01); *A61F 2220/0008* (2013.01); *A61F 2220/0033* (2013.01); *A61F 2230/0091* (2013.01)
(58) Field of Classification Search
CPC ............ A61F 2/2418; A61F 2220/0008; A61F 2/2439; A61F 2/2457; A61F 2230/0091; A61F 2220/0033
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,423,730 A | 1/1984 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — Richard Louis
(74) *Attorney, Agent, or Firm* — Lerner, David, Littenberg, Krumholz & Mentlik, LLP

(57) ABSTRACT

A prosthetic heart valve includes a collapsible and expandable stent having an outflow end and an inflow end, a plurality of commissure features attached to the stent, a plurality of anchoring features disposed on legs of the stent, the plurality of anchoring features being coupleable to a delivery device for repositioning, and a valve assembly disposed within the stent. The anchoring features may be configured to attach to heart tissue to help secure the prosthetic heart valve in an operating position.

13 Claims, 8 Drawing Sheets

(56) References Cited

U.S. PATENT DOCUMENTS

| | | |
|---|---|---|
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,077,297 A | 6/2000 | Robinson et al. |
| 6,083,257 A * | 7/2000 | Taylor ................. A61F 2/90 623/1.46 |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0065385 A1 * | 4/2003 | Weadock ................. A61F 2/07 623/1.23 |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0049692 A1 * | 3/2005 | Numamoto ........... A61F 2/2418 623/1.24 |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0149360 A1 | 7/2006 | Schwammenthal et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 * | 10/2006 | Solem ................. A61F 2/246 623/2.18 |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 * | 2/2010 | Alon ................. A61F 2/2418 623/2.11 |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |

(56) References Cited

U.S. PATENT DOCUMENTS

| | | | |
|---|---|---|---|
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0224678 A1 | 9/2011 | Gabbay | |
| 2012/0303116 A1* | 11/2012 | Gorman, III | A61F 2/2418 623/2.11 |
| 2013/0190861 A1* | 7/2013 | Chau | A61F 2/2418 623/2.18 |
| 2014/0379074 A1* | 12/2014 | Spence | A61F 2/2418 623/2.11 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008070797 A2 | 6/2008 |
| WO | 2010008548 A2 | 1/2010 |
| WO | 2010008549 A1 | 1/2010 |
| WO | 2010051025 A1 | 5/2010 |
| WO | 2010087975 A1 | 8/2010 |
| WO | 2010096176 A1 | 8/2010 |
| WO | 2010098857 A1 | 9/2010 |

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Percutaneous aortic valve replacement: resection before implantation, 836-840, Quaden, Rene et al., European J. of Cardio-thoracic Surgery, 27 (2005).
Ruiz, Carlos, Overview of PRE-CE Mark Transcatheter Aortic Valve Technologies, Euro PCR—dated May 25, 2010.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243, filed Sep. 20, 2010.
U.S. Appl. No. 29/375,260, filed Sep. 20, 2010.

* cited by examiner

TRANSAPICAL MITRAL VALVE REPLACEMENT

CROSS-REFERENCES TO RELATED APPLICATIONS

The present application claims the benefit of the filing date of U.S. Provisional Application No. 61/771,439, filed Mar. 1, 2013, the disclosure of which is hereby incorporated herein by reference.

BACKGROUND OF THE INVENTION

The present invention relates to heart valve replacement and, in particular, to collapsible prosthetic heart valves. More particularly, the present invention relates to devices and methods for repositioning and anchoring collapsible prosthetic heart valves during the deployment procedure.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from some shortcomings. In conventional collapsible heart valves, the stent is usually anchored within the native valve annulus via the radial force of the expanding stent against the native valve annulus. If the radial force is too high, damage may occur to heart tissue. If, instead, the radial force is too low, the heart valve may prolapse or migrate, for example, into the left ventricle, requiring emergency surgery to remove the displaced valve. Because this radial anchoring partly depends on the presence of calcification or plaque in the native valve annulus, it may be difficult to properly anchor the valve in locations where plaque is lacking (e.g., the mitral valve annulus). Additionally, in certain locations, such as for mitral valve applications, the heart valve may require a lower profile so as not to interfere with surrounding tissue structures. Such a low profile makes it difficult for the valve to remain in place.

Moreover, it is not possible at this time, using available collapsible heart valves and delivery devices, to determine whether a valve assembly will function as intended without full deployment of the heart valve. However, due to anatomical variations between patients, a fully deployed heart valve may need to be removed from the patient if it appears that the valve is not functioning properly. Removing a fully deployed heart valve increases the length of the procedure and the risk of damage to surrounding tissue.

In view of the foregoing, there is a need for further improvements to the devices, systems, and methods for transcatheter delivery and anchoring of collapsible prosthetic heart valves, and in particular, self-expanding prosthetic heart valves. More particularly, a need exists for an arrangement that will enable the functioning of the valve to be ascertained prior to full deployment. Among other advantages, the present invention may address one or more of these needs.

SUMMARY OF THE INVENTION

In some embodiments, a prosthetic heart valve includes a collapsible and expandable stent having an outflow end and an inflow end. The outflow end includes a plurality of legs movable between a substantially straight configuration and a relaxed configuration capable of grasping heart tissue. A plurality of commissure features may be disposed on the stent and a plurality of anchoring features may be disposed on respective ones of the plurality of legs, the plurality of anchoring features being coupleable to a delivery device. A collapsible and expandable valve assembly may be disposed within the stent.

In some examples, each of the legs may be biased to move to a curled configuration in a relaxed configuration. Each of the legs may be configured to curl about the chordae tendinea in the curled configuration. The curled configuration may be a helical configuration, the legs being biased to move to the helical configuration in the relaxed configuration. The plurality of anchoring features may include at least one C-shaped barb. The outflow end of the stent may have an expanded circumference, and the inflow end of the stent has a flared portion, the flared portion having an expanded circumference that is larger than the expanded circumference of the outflow end of the stent. The heart valve may be a mitral valve. The valve assembly may include a plurality of leaflets. The device may further include sutures connecting the plurality of leaflets to the plurality of commissure features.

In some embodiments, a catheter for delivering a prosthetic heart valve to a deployment site in a patient may include an outer sheath, a plurality of wires disposed within the outer sheath, each of the plurality of wires terminating in a coupler operable to connect to a portion of the prosthetic heart valve, and a plurality of sleeves, each one of the plurality of sleeves being disposed about one of the plurality of wires.

In some examples, the plurality of wires may be formed from a shape-memory material. The coupler may be a hook. The plurality of wires may be formed from a suture material. The coupler may be a suture loop. Each of the plurality of sleeves may be translatable relative to the plurality of wires. The catheter may further include an inner tube for accepting the plurality of wires.

In some embodiments, a method of deploying a prosthetic heart valve at a target site, the prosthetic heart valve including a collapsible and expandable stent having an outflow end and an inflow end, and a collapsible and expandable valve assembly disposed within the stent may include (i) introducing a delivery device to the target site, the delivery device including an outer sheath, the prosthetic heart valve being disposed within the outer sheath, a plurality of wires disposed within the outer sheath, each of the plurality of wires terminating in a coupler connected to the heart valve, and a plurality of sleeves, each one of the plurality of sleeves being disposed about one of the plurality of wires, (ii) withdrawing the sheath a first distance to partially deploy the prosthetic heart valve at the target site such that the valve assembly is partially deployed at the first distance and can function as intended while the outflow end of the stent is coupled to the plurality of wires, and (iii) pulling at least one of the plurality of wires to reposition the heart valve.

In some examples, the method may further include withdrawing the plurality of sleeves to expose the plurality of wires. The method may further include decoupling the couplers from the heart valve. The plurality of wires may include a suture material and the decoupling step may include cutting the suture material. The coupler may include a hook and the decoupling step may include detaching the hook from the heart valve.

BRIEF DESCRIPTION OF THE DRAWINGS

Various embodiments of the present invention are disclosed herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

Blood flows through the mitral valve from the left atrium to the left ventricle. As used herein, the term "inflow," when used in connection with a prosthetic mitral heart valve, refers to the end of the heart valve closest to the left atrium when the heart valve is implanted in a patient, whereas the term "outflow," when used in connection with a prosthetic heart valve, refers to the end of the heart valve closest to the left ventricle when the heart valve is implanted in a patient. When used in connection with devices for delivering a prosthetic heart valve into a patient, the terms "trailing" and "leading" are to be taken as relative to the user of the delivery devices. "Trailing" is to be understood as relatively close to the operator, and "leading" is to be understood as relatively farther away from the operator.

Figure 1:
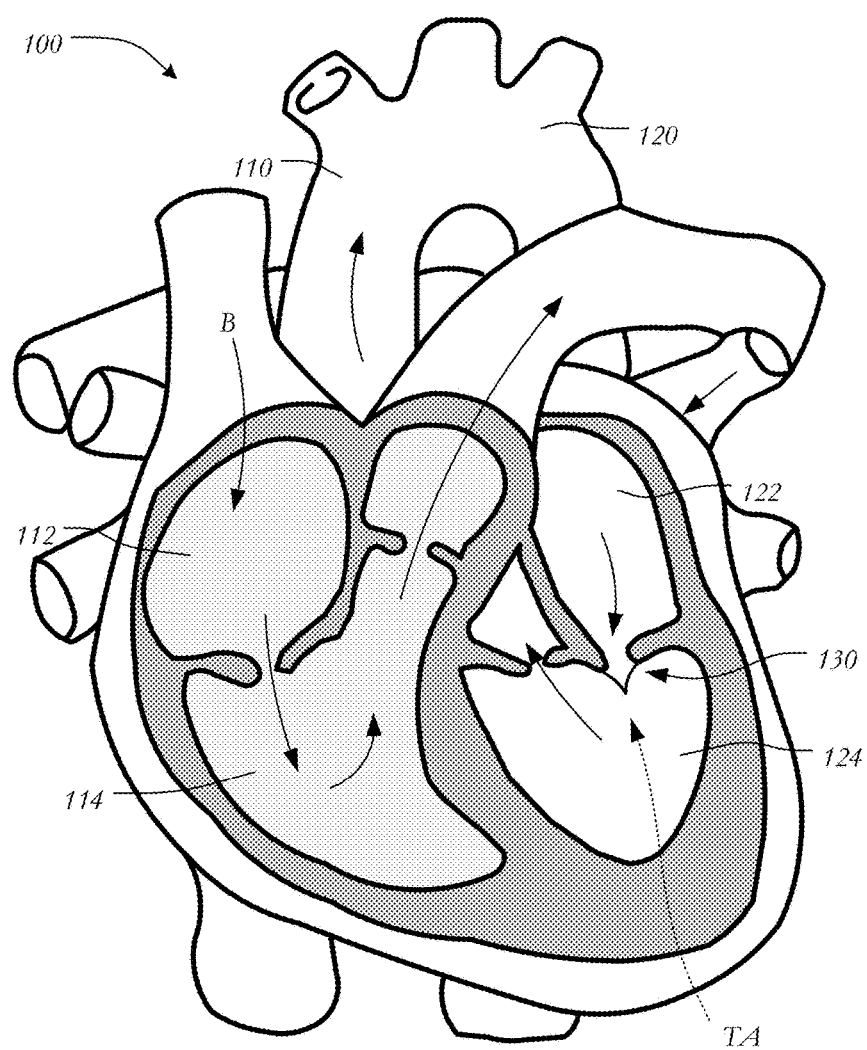
FIG. 1 is a schematic representation of a human heart showing a transapical delivery approach.

FIG. 1 is a schematic representation of a human heart 100. The human heart includes two atria and two ventricles: a right atrium 112 and a left atrium 122, and a right ventricle 114 and a left ventricle 124. As illustrated in FIG. 1, the heart 100 further includes an aorta 110, and an aortic arch 120. Disposed between the left atrium and the left ventricle is the mitral valve 130. The mitral valve 130, also known as the bicuspid valve or left atrioventricular valve, is a dual-flap that opens as a result of increased pressure from the left atrium as it fills with blood. As atrial pressure increases above that of the left ventricle, the mitral valve opens and blood passes toward the left ventricle. Blood flows through heart 100 in the direction shown by arrows "B".

A dashed arrow, labeled as "TA", indicates a transapical approach of implanting a prosthetic heart valve, in this case to replace a mitral valve. In transapical delivery, a small incision is made between the ribs and into the apex of the left ventricle 124 to deliver the prosthetic heart valve to the target site.

Figure 2:
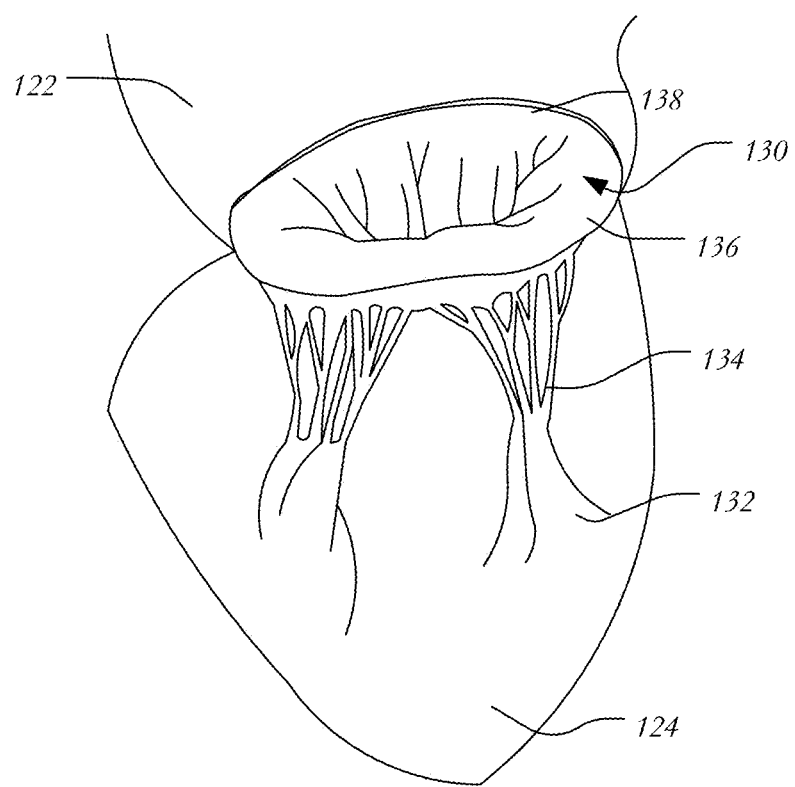
FIG. 2 is a schematic representation of a native mitral valve and associated structures.

FIG. 2 is a more detailed schematic representation of a native mitral valve 130 and its associated structures. As previously noted, mitral valve 130 includes two flaps or leaflets, a posterior leaflet 136 and an anterior leaflet 138, disposed between left atrium 122 and left ventricle 124. Cord-like tendons known as chordae tendineae 134 connect the two leaflets 136, 138 to the medial and lateral papillary muscles 132. During atrial systole, blood flows from the left atrium to the left ventricle down the pressure gradient. When the left ventricle contracts in ventricular systole, the increased blood pressure in the chamber pushes the mitral valve to close, preventing backflow of blood into the left atrium. Since the blood pressure in the left atrium is much lower than that in the left ventricle, the flaps attempt to evert to the low pressure regions. The chordae tendineae prevent the eversion by becoming tense, thus pulling the flaps and holding them in the closed position.

Figure 3:
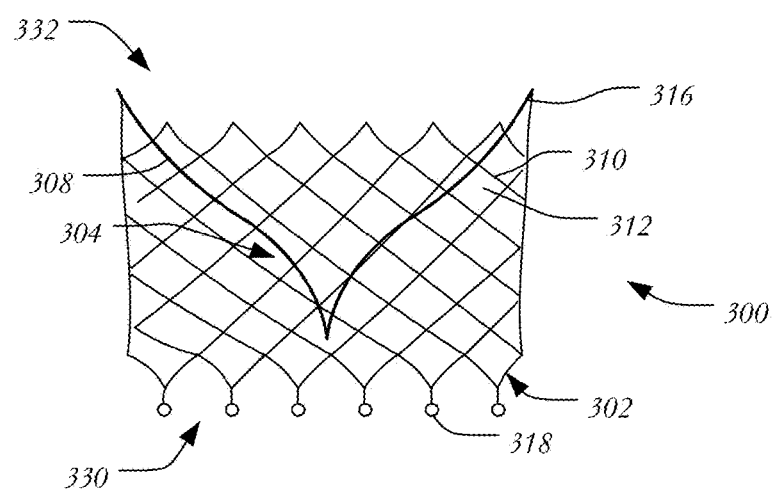
FIG. 3 is a schematic representation of a prosthetic mitral valve in accordance with one embodiment of the present invention.

FIG. 3 is a schematic representation of a prosthetic mitral valve 300 in accordance with one embodiment of the present disclosure. The prosthetic heart valve 300 is a collapsible prosthetic heart valve designed to replace the function of the native mitral valve of a patient. Examples of collapsible prosthetic heart valves are described, generally, in International Patent Application Publication No. WO/2009/042196; U.S. Pat. No. 7,018,406; and U.S. Pat. No. 7,329,278, the disclosures of all of which are hereby incorporated herein by reference.

Prosthetic heart valve 300 includes an expandable stent 302 which may be formed from biocompatible materials that are capable of self-expansion, such as, for example, shape memory alloys such as nitinol. Stent 302 extends from an outflow end 330 to an inflow end 332. Heart valve 300 may be substantially cylindrical, or may slightly taper outwardly from the outflow end 330 to the inflow end 332. As discussed above, mitral valve 300 may have a low profile so as not to interfere with atrial function.

Stent 302 may include a plurality of struts 310 that form cells 312 connected to one another in one or more annular rows around the stent. The cells 312 may all be of substantially the same size around the perimeter and along the length of stent 312. Alternatively, cells 312 near the inflow end 332 may be larger than the cells near the outflow end 330.

One or more anchors 318 may be provided at the outflow end 330 of stent 302, the anchors being sized and shaped to cooperate with complementary structures provided on a deployment device. The engagement of anchors 318 with the structures on the deployment device helps maintain prosthetic heart valve 300 in an assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment. The anchors 318 may also be useful in repositioning heart valve 300 and affixing the heart valve to tissue after full deployment, as will be discussed in more detail below with reference to FIGS. 5A-8.

The stent 302 may also include a plurality of commissure features 316 at which the leaflet commissures are attached to the stent, for example by sutures (not shown). The commissure features 316 may lie at the intersection of four cells 312, two of the cells being adjacent one another in the same annular row, and the other two cells being in different annular rows and lying in end-to-end relationship with one another. Preferably, commissure features 316 are positioned near the inflow end 332 of heart valve 300. Commissure features 316 optionally may include one or more eyelets which facilitate the attachment of the leaflet commissures to the stent.

The prosthetic heart valve 300 includes a valve assembly 304 disposed within stent 302. Valve assembly 304 may be secured to stent 302 by suturing to struts 310, which constitute the cells 312 of the stent, by suturing to the commissure features 316 of the stent, or by other attachment mechanisms. Valve assembly 304 may include a cuff (not shown) and a plurality of leaflets 308 which collectively function as a one-way valve by coapting with one another. In the example shown, heart valve 300 is intended to replace the native mitral valve, which as described above includes two leaflets; heart valve 300 is therefore illustrated with a pair of leaflets 308. However, it will be appreciated that the prosthetic heart valves according to this aspect of the invention may have a greater number of leaflets and commissure features. Both the cuff and the leaflets 308 may be wholly or partly formed of any suitable biological material, such as bovine or porcine pericardium, or polymers, such as PTFE, urethanes and the like.

The prosthetic heart valve described above may be used to replace a native heart valve, such as the mitral valve, a surgical heart valve or a heart valve that has undergone a surgical procedure. The prosthetic heart valve may be delivered to the desired site (e.g., near a native mitral annulus) using any suitable delivery device, including the delivery devices described in detail below. During delivery, the prosthetic heart valve is disposed inside the delivery device in the collapsed condition. The delivery device may be introduced into a patient using a transapical or other percutaneous approach. Once the delivery device has reached the target site, the user may deploy the prosthetic heart valve. The prosthetic heart valve may be held to the delivery device by anchors, as will be described in more detail below. Upon deployment, the prosthetic heart valve expands into secure engagement within the native anatomic structure, such as the mitral valve annulus. When the prosthetic heart valve is properly positioned inside the patient, it works as a one-way valve, allowing blood to flow in one direction and preventing blood from flowing in the opposite direction.

In a prosthetic heart valve, the valve assembly 304 may be spaced from the outflow end 330 of the stent 302 by a distance that enables deployment of the heart valve by an amount sufficient for the leaflets of the prosthetic valve to operate as intended, while the outflow end 330 of the stent remains captured by the delivery device. By configuring the prosthetic heart valve in this manner, the user can determine whether the valve leaflets are properly positioned relative to the native valve annulus, and whether the valve is functioning properly. If the user determines that the positioning and operation of the valve are acceptable, the remainder of the valve may be deployed. However, if it is determined that the leaflet position is improper or that the valve is not functioning properly, the user may resheath the valve and either reposition it for redeployment, or remove it entirely from the patient. This can be particularly important in very high risk patients who would typically be recipients of these types of valves because of the nature of their condition and the impact that may have on the shape and/or condition of the native valve and valve annulus.

Figure 4:
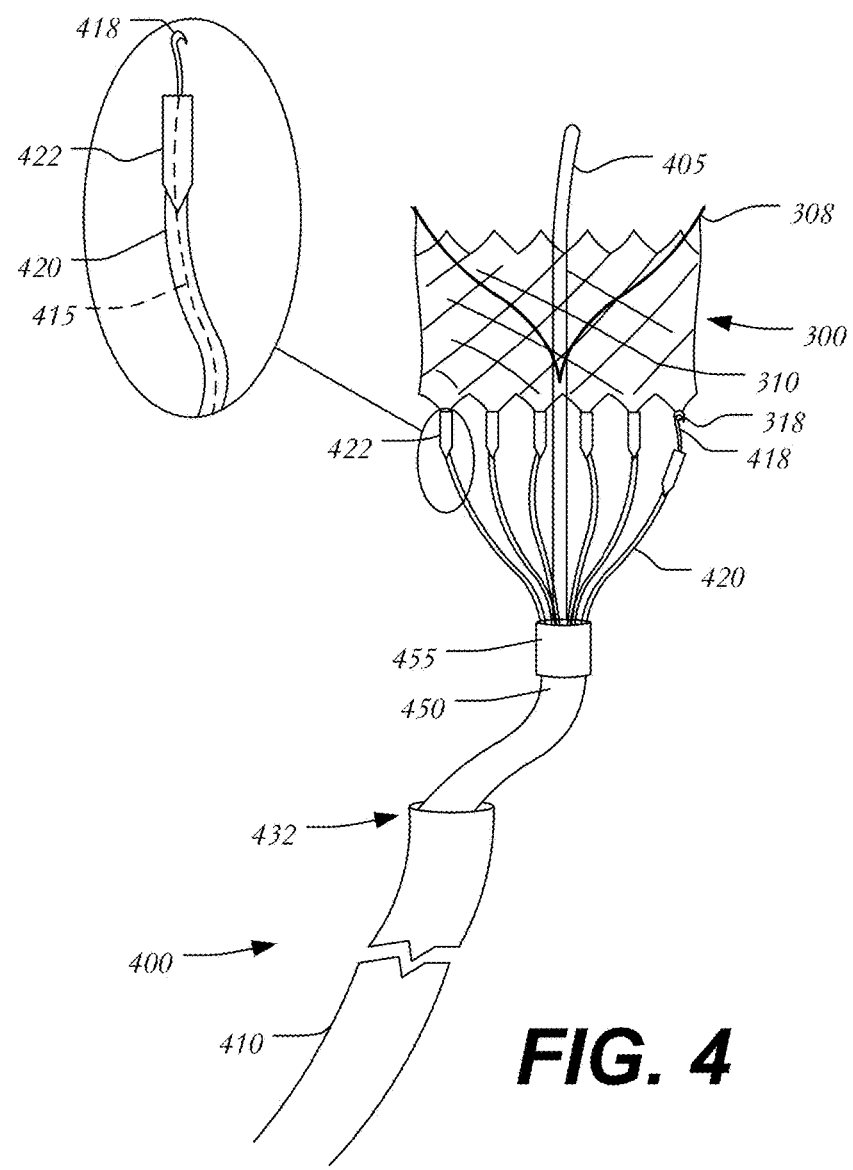
FIG. 4 is a fragmentary side elevational view of a delivery device for delivering the valve of FIG. 3.

FIG. 4A is a fragmentary side elevational view of a delivery device 400 for delivering heart valve 300. Delivery device 400 may include a guidewire 405, an outer sheath 410, a plurality of wires 415 and sleeves 420.

Sheath 410 may extend from a leading end 432 to a trailing end (not shown) and may be sized to accept heart valve 300 in the collapsed condition for delivery. Guidewire 405 may extend through sheath 410 and through heart valve 300 when the heart valve is loaded in delivery device 400. Guidewire 405 may include additional elements (not shown) for accepting or coupling the collapsed heart valve 300 thereto.

A plurality of wires 415 may also be disposed within sheath 410. Each wire 415 may extend through sheath 410 from the trailing end of the sheath to a coupler 418 at its leading end. Wires 415 may be formed of a biologically compatible metal such as any of the metals used in constructing struts 310 of heart valve 300. The metal may be a shape-memory wire that is biased radially outward from sheath 410 to facilitate a recapture process should one become necessary. Alternatively, wires 415 may be formed of a suture or polymeric thread. Wires 415 should be sufficiently flexible to allow for guiding and delivery within the anatomy, yet strong enough to enable repositioning of the heart valve 300 as will be described below. The couplers 418 at the ends of wires 415 are adapted to mate with anchors 318 of heart valve 300. Each coupler 418 may be in the form of a metallic hook, clasp or pin that engages with an anchor 318. Alternatively, each coupler 418 may be in the form of a suture or thread loop tied around an anchor 318.

As seen in FIG. 4A, each wire 415 may be disposed within a sleeve 420 having an enlarged crown 422 for accepting anchors 318 of heart valve 300. Sleeves 420 may be formed as plastic or polymeric tubes capable of preventing the couplers 418 from becoming disengaged from anchors 318 during delivery and/or repositioning. Each sleeve 420 may be disposed over a wire 415 so as to be translatable relative to the wire. One of the sleeves 420 has been retracted over wire 415 in FIG. 4A to reveal the structure of a coupler 418 and its connection to an anchor 318.

FIG. 4A further illustrates an optional inner tube 450 disposed within outer sheath 410 for accepting wires 415. Inner tube 450 may be useful in bundling the wires 415 and preventing them from becoming entangled during delivery and repositioning of valve 300. Inner tube 450 may be capable of telescoping within outer sheath 410.

To use delivery device 400 for delivering a prosthetic heart valve, such as mitral valve 300, the operator may advance the delivery catheter into the patient's heart using the transapical approach shown in FIG. 1. Once in position, the guidewire 405 may be held in place while outer sheath 410 and inner tube 450 are retracted to expose collapsible heart valve 300 and sleeves 420. Once outer sheath 410 has been retracted, heart valve 300 may begin to expand, as shown in FIG. 4A. At this position, heart valve 300 may be partially expanded such that leaflets 308 are fully operational and the valve assembly 304 may be tested for proper functionality with each anchor 318 of the heart valve still mated with a coupler 418 of delivery device 400. If the operator has determined that the heart valve 300 is in a suitable position and functioning properly, the catheter may be decoupled from the heart valve and removed from the patient. This may be accomplished by retracting sleeves 420 to expose wires 415. If the wires 415 are metal, couplers 418 may be unhooked or otherwise decoupled from anchors 318 and retracted within outer sheath 410. If the wires 415 are made of a suture material, they may be severed, leaving the fully-functional heart valve 300 within the native valve annulus. Delivery catheter 400 may then be withdrawn from the body.

If, however, the operator determines that an adjustment is necessary, he may pull on any one of the wires 415 to slightly reposition the heart valve within the native valve annulus. Two or more wires 415 may be actuated simultaneously or the wires may be actuated one at a time. If the heart valve 300 is incapable of proper operation despite multiple repositioning attempts using wires 415, inner tube 450 and outer sheath 410 may be advanced over wires 415 to recapture heart valve 300 and remove it from the patient.

FIG. 4B illustrates a variation of the delivery device of FIG. 4A and includes many of the same elements. Specifically, delivery device 400' may include a guidewire 405, an outer sheath 410, a plurality of wires 415, an inner tube 450 and sleeves 420'. As in FIG. 4B, however, delivery device 400' is configured such that each sleeve 420' receives a plurality of terminal legs 313 of stent 300' therein. Moreover, it will be appreciated that each sleeve 420' includes an enlarged crown portion 422' and may include an enlarged coupler 418' capable of mating with complementary features disposed on each terminal leg 313 of stent 300'. Alternatively, delivery device 400' may include multiple couplers 418' attached to each wire 415, one coupler 418' for each terminal leg 313. In at least some examples of this embodiment, each sleeve 420' is configured to receive three terminal legs 313 of stent 300'. Thus, in a stent 300' having nine cells around the perimeter, delivery device 400' may include three sleeves 420'. Utilizing less sleeves 420' and wires 415 may simply the deployment process and result in quicker operation.

Figure 5A:
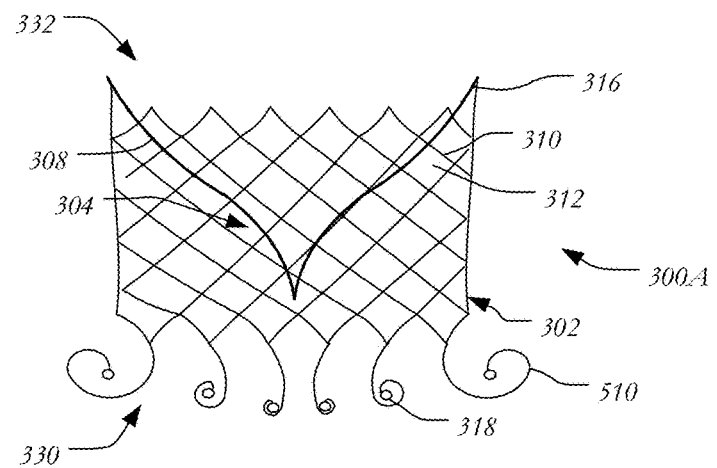
FIG. 5A is a schematic representation of a prosthetic mitral valve having elongated legs in accordance with a second embodiment of the present invention.
Figure 5B:
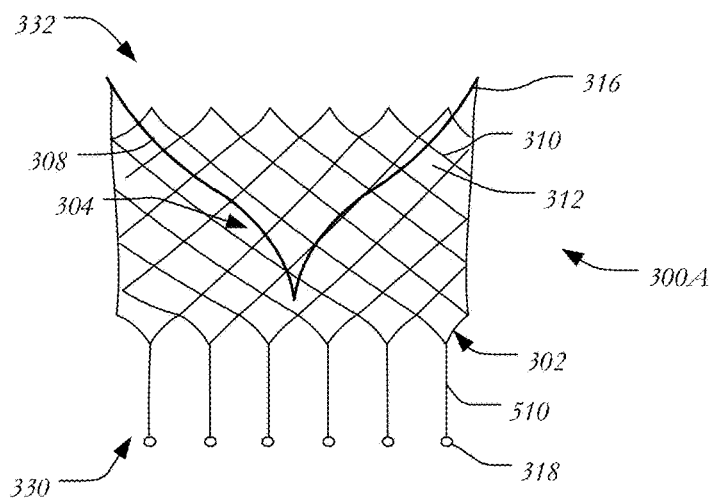
FIG. 5B is a schematic representation of the prosthetic mitral valve of FIG. 5A with the elongated legs in the curled position.
Figure 5C:
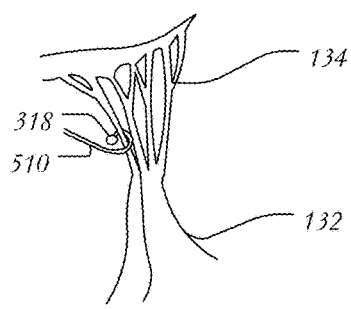
FIG. 5C is a schematic representation showing the elongated legs of the prosthetic mitral valve of FIG. 5A curled about the chordae tendineae.

FIGS. 5A-C are schematic representations of a prosthetic mitral valve 300A in accordance with a second embodiment of the present invention. Heart valve 300A is similar to heart valve 300 described above, and includes a stent 302 and a valve assembly 304 having a pair of leaflets 308. Heart valve 300A further includes certain features for aiding in properly anchoring the heart valve in the native valve annulus.

As seen in FIG. 5A, the struts near outflow end 330 of stent 302 form elongated legs 510. Though FIG. 5A illustrates all of the struts at outflow end 330 forming elongated legs 510, it will be understood that any number of elongated legs 510 may be included in stent 302, including one, two, three, four or more elongated legs. Any or all of the elongated legs 510 may end with an anchor 318 for mating with the couplers 418 of wires 415 of the delivery device described above. FIG. 5A illustrates elongated legs 510 in a relaxed state in which the legs have a curled configuration. This is the shape to which the legs 510 are biased when removed from sleeves 420. When disposed within sleeves 420 during delivery and repositioning, legs 510 may have a substantially straight configuration, as shown in FIG. 5B.

As mitral valve 300A is delivered to an appropriate implantation site and deployed, the elongated legs 510 thereof will initially be disposed within sleeves 420, and will thus have a substantially straight configuration. However, elongated legs 510 may be formed from a shape memory alloy that will return to a relaxed state when removed from sleeves 420. Therefore, as sleeves 420 are removed from legs 510, the legs may revert to the curled configuration shown. In addition to the anchoring attributable to the radial force exerted by the stent 302 of valve 300A, this curled configuration may provide extra anchoring of the valve in the native valve annulus by hooking onto the chordae tendineae. FIG. 5C illustrates this coupling of the elongated legs 510 to the chordae tendineae 134. Elongated legs 510 that do not terminate in anchors 318 may include atraumatic tips that curl around the chordae tendineae 134 in addition to portions of the medial or lateral papillary muscles 132 without damaging these structures. Alternatively, each elongated leg 510 that does not terminate in an anchor 318 may terminate in a sharp barb that punctures the native valve leaflet or surrounding tissue for additional anchoring.

Figure 6A:
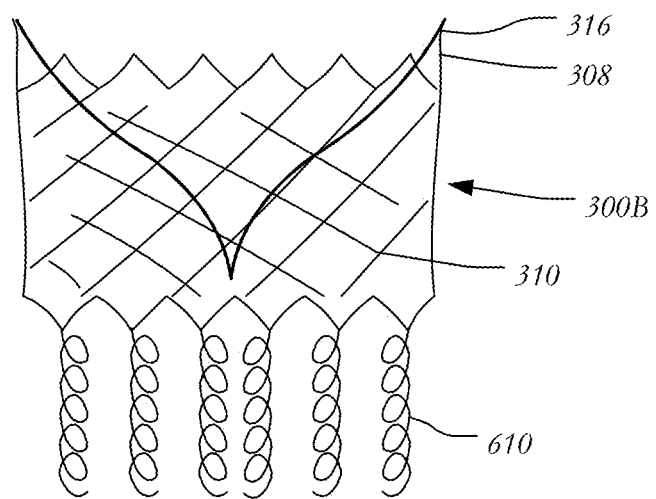
FIG. 6A is a schematic representation of a prosthetic mitral valve having helical struts in accordance with a third embodiment of the present invention.
Figure 6B:
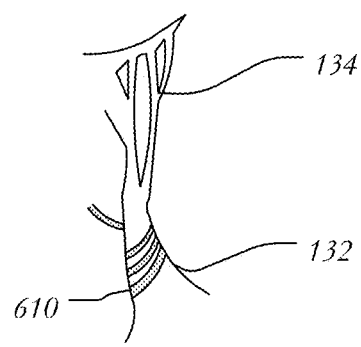
FIG. 6B is a schematic representation showing the helical struts of the prosthetic mitral valve of FIG. 6A wrapped about the papillary muscles.

FIG. 6A is a schematic representation of a prosthetic mitral valve 300B in accordance with a third embodiment of the present invention. Instead of the curling elongated legs 510 of prosthetic valve 300A, the struts near outflow end 330 of stent 302 may terminate in spiral or helical struts 610. Struts 610 may have a helical configuration when in the relaxed state, much the same as the elongated legs 510 of valve 300A have a curled configuration in the relaxed state. However, when confined within sleeves 420, struts 610 may be substantially straight, as shown in FIG. 5A. After deployment of valve 300B and retraction of sleeves 420, struts 610 may return to their relaxed helical configuration, enabling them to wrap around the chordae tendineae 134 or the papillary muscles 132, as shown in FIG. 6B.

Figure 7A:
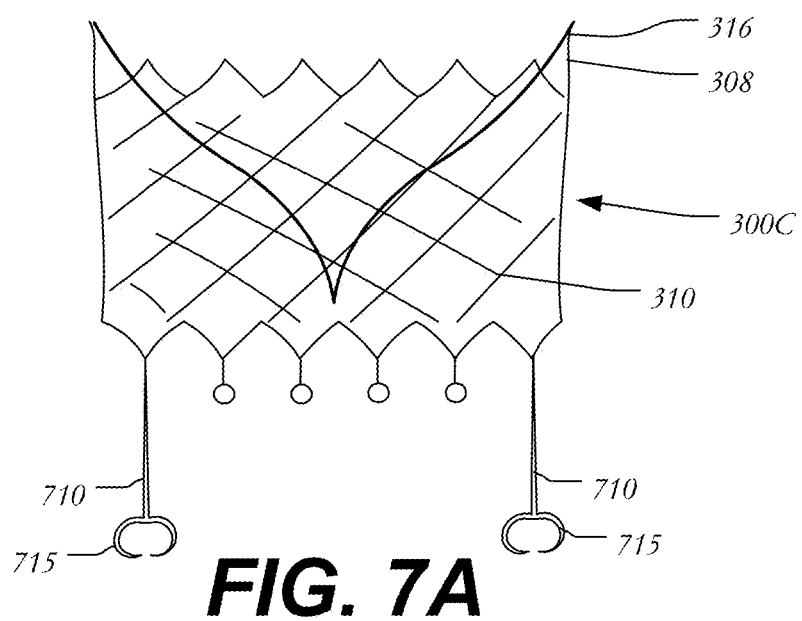
FIG. 7A is a schematic representation of a prosthetic mitral valve having C-shaped barbs in accordance with a fourth embodiment of the present invention.
Figure 7B:
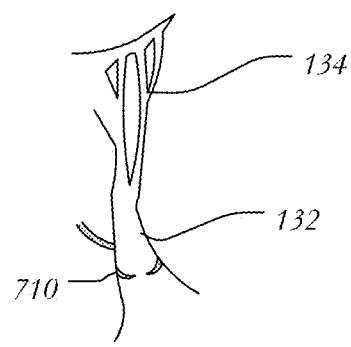
FIG. 7B is a schematic representation of the C-shaped barbs of the prosthetic mitral valve of FIG. 7A cinching the papillary muscles.

Instead of curling elongated legs or helical struts, the stent 302 of a prosthetic mitral valve 300C may include C-shaped barbs 710 on selected struts, as shown in FIG. 7A, while the rest of the struts may include the anchors 318 of mitral valve 300 described above. Each C-shaped barb 710 may include two or more piercing points 715 for capturing the chordae tendineae 134 or papillary muscles 132. FIG. 7B is a schematic representation of the C-shaped barb of FIG. 7A cinching the papillary muscles 132. By cinching papillary muscles or chordae tendineae using C-shaped barbs 710 on opposite lateral sides of heart valve 300C, anchoring within the native valve annulus may be improved.

Figure 8:
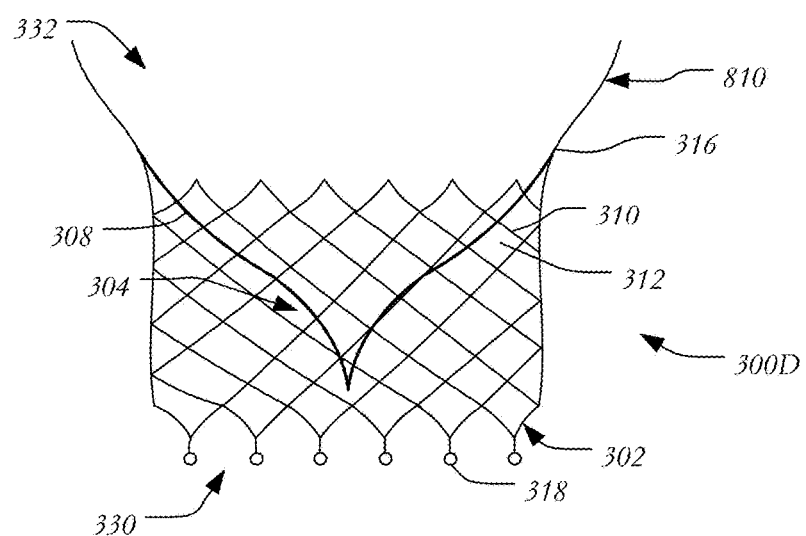
FIG. 8 is a schematic representation of a prosthetic mitral valve having a flared inflow end portion in accordance with a fifth embodiment of the present invention.

In addition to adding anchoring features to the outflow end 330 of the prosthetic heart valves described herein, certain anchoring features may be added near the inflow end 332 of the valve. FIG. 8 is a schematic representation of a prosthetic mitral valve 300D having a flared inflow end portion 810 in accordance with another embodiment of the present invention. In this embodiment, stent 302 includes an outwardly flared portion 810 that extends into the left atrium and is biased radially outwardly. When valve 300D is disposed within the native valve annulus, flared portion 810 enables stent 302 to sit within the annulus and prevents the stent from slipping into, for example, the left ventricle when blood flows through valve assembly 304.

It will be appreciated that the various dependent claims and the features set forth therein can be combined in different ways than presented in the initial claims. For example, a prosthetic heart valve may include both a flared inflow portion as well as any of the various anchoring features near the outflow end discussed above. Additionally, a prosthetic heart valve may include any number of anchoring features or combinations thereof. For example, a prosthetic heart valve may include alternating curling legs and helical legs. Alternatively, a prosthetic heart valve may include struts of varying lengths that include these features, some for coupling to the chordae tendineae, others for coupling to the papillary muscles, and still others for coupling to the native valve leaflets. It will be appreciated that any of the features described in connection with individual embodiments may be shared with others of the described embodiments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for heart valve replacement, the system comprising:
   a catheter including:
      an outer sheath;
      a plurality of wires disposed within the outer sheath, each of the plurality of wires terminating in at least one hook-shaped coupler; and
      a plurality of sleeves, each one of the plurality of sleeves being disposed about one of the plurality of wires; and
   a prosthetic heart valve including:
      a collapsible and expandable stent having an outflow end and an inflow end, the outflow end including a plurality of legs, each of the plurality of legs extending between an attached end coupled to the stent, and a free end unattached to the stent, the plurality of legs being movable between a substantially straight configuration and a curled, relaxed configuration extending away from the outflow end such that a first distance between the inflow end and the free end is greater than a second distance between the inflow end and the attached end, the plurality of legs being capable of grasping heart tissue in the relaxed configuration; and
      a plurality of closed, circular anchoring features, each anchoring feature being disposed on the free end of respective ones of the plurality of legs, each of the plurality of anchoring features being coupleable to a hook-shaped coupler of the catheter.

2. The system of claim 1, wherein the plurality of wires are formed from a shape-memory material.

3. The system of claim 1, wherein the at least one coupler includes a hook.

4. The system of claim 1, wherein the plurality of wires are formed from a suture material.

5. The system of claim 1, wherein the at least one coupler includes a suture loop.

6. The system of claim 1, wherein each of the plurality of sleeves is translatable relative to the plurality of wires.

7. The system of claim 1, further comprising an inner tube for accepting the plurality of wires.

8. The system of claim 1, wherein each of the at least one coupler is configured to mate with a plurality of legs of the prosthetic heart valve.

9. A method of deploying a prosthetic heart valve at a target site, the prosthetic heart valve including a collapsible and expandable stent having an outflow end and an inflow end, the outflow end including a plurality of legs, each of the plurality of legs extending between an attached end coupled to the stent, and a free end unattached to the stent, the plurality of legs being movable between a substantially straight configuration and a relaxed configuration extending away from the outflow end such that a first distance between the inflow end and the free end is greater than a second distance between the inflow end and the attached end, and a plurality of anchoring features, each anchoring feature being disposed on the free end of respective ones of the plurality of legs, each of the plurality of anchoring features being coupleable to a coupler of the catheter, and a collapsible and expandable valve assembly disposed within the stent, the method comprising:
   introducing a delivery device to the target site, the delivery device including an outer sheath, the prosthetic heart valve being disposed within the outer sheath, a plurality of wires disposed within the outer sheath, each of the plurality of wires terminating in a coupler directly connected to one of the anchoring features of the heart valve, and a plurality of sleeves, each one of the plurality of sleeves being disposed about one of the plurality of wires;
   withdrawing the sheath a first distance to partially deploy the prosthetic heart valve at the target site such that the valve assembly is partially deployed at the first distance and can function as intended while the anchoring features are coupled to the plurality of wires; and
   pulling at least one of the plurality of wires to reposition the heart valve.

10. The method of claim 9, further comprising withdrawing the plurality of sleeves to expose the plurality of wires.

11. The method of claim 9, further comprising decoupling the couplers from the heart valve.

12. The method of claim 11, wherein the plurality of wires includes a suture material and the decoupling step includes cutting the suture material.

13. The method of claim 11, wherein the coupler includes a hook and the decoupling step includes detaching the hook from the heart valve.

* * * * *